US006942663B2

(12) United States Patent
Vargas et al.

(10) Patent No.: US 6,942,663 B2
(45) Date of Patent: Sep. 13, 2005

(54) LASER TREATMENT OF CUTANEOUS VASCULAR LESIONS

(75) Inventors: Gracie Vargas, Galveston, TX (US); Jennifer K. Barton, Tucson, AZ (US); Eric K. Chan, Lexington, MA (US); Thomas E. Milner, Austin, TX (US); Ashley J. Welch, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/385,195

(22) Filed: Mar. 10, 2003

(65) Prior Publication Data

US 2004/0019120 A1 Jan. 29, 2004

Related U.S. Application Data

(60) Provisional application No. 60/363,726, filed on Mar. 12, 2002.

(51) Int. Cl.[7] ........................ A61B 18/14; A61K 47/06; A61K 47/46; A61K 31/40
(52) U.S. Cl. ............................. 606/49; 606/41; 606/50; 514/21; 514/63; 514/567; 424/94.4; 424/195.11
(58) Field of Search ............................. 606/49, 41, 50; 514/21, 63, 567; 424/94.4, 195.11

(56) References Cited

U.S. PATENT DOCUMENTS

| | | | | |
|---|---|---|---|---|
| 5,599,342 A | * | 2/1997 | Hsia et al. ...................... | 606/9 |
| 5,703,051 A | * | 12/1997 | Berliner et al. ............... | 514/21 |
| 6,228,082 B1 | * | 5/2001 | Baker et al. ................... | 606/49 |
| 6,275,726 B1 | | 8/2001 | Chan et al. ................... | 600/476 |
| 6,364,872 B1 | * | 4/2002 | Hsia et al. ...................... | 606/9 |
| 6,702,808 B1 | * | 3/2004 | Kreindel ........................ | 606/9 |
| 6,733,435 B2 | * | 5/2004 | Canedo .......................... | 600/9 |

OTHER PUBLICATIONS

Barton, "Predicting Dosimetry for Laser Coagulation of in vivo Cutaneous Blood Vessels," Doctoral Dissertation, The University of Texas at Austin, 1998.
Boergen et al., "Experimental studies on argon laser coagulation of small blood vessels," *Modern Problems in Ophthalmology*, 20:174–183 1979.
Boergen et al., "Experimental studies on controlled closure of small vessels by laser irradiation," *Lasers in Surgery, Medicine, and Biology Proceedings*, 15–1—15–9, 1977.
Cain and Noojin, "A comparison of various probit methods for analyzing yes/no data on a log scale," Report AL/OE–TR–1996–0102, U.S.A.F. Armstrong Laboratory, Brooks Air Force Base, TX, 1996.
Goldman, "Leg Veins: Pathogenesis, Sclerotherapy, and Lasers," Chapter 13, pp. 165–179, in: *Management and treatment of benign cutaneous vascular lesions*, Tan, (ed.), Lea & Febiger, Philadelphia, 1992.

Gorish et al., "Temperature measurement of laser irradiated mesenterial blood vessels of the rabbit," In: *Laser in Medizin und Biologie* (*Lasers in Medicine and Biology*), 8–1—8–8, 1977.
Izatt et al., "In vivo bidirectional color Doppler flow imaging of picoliter blood volumes using optical coherence tomography," *Optics Letters*, 22:1439–1441, 1997.
Kimel et al., "Differential vascular to laser photothermolysis," *Journal of Investigative Dermatology*, 103:693–700, 1994.
Lanigan and Cotterill, "Psychological disabilities amongst patients with port wine stains," *British Journal of Dermatology*, 121:209–215, 1989.
Masciarelli, "Living with a port–wine birthmark," Chapter 14, pp. 180–185, in: *Management and treatment of benign cutaneous vascular lesions*, Tan (ed.), Lea & Febiger, Philadelphia, 1992.
Mulliken, "The classification of vascular birthmarks," Chapter 1, pp. 1–23, in *Management and treatment of benign cutaneous vascular lesions*, Tan (ed.), Lea & Febiger, Philadelphia 1992.
Papenfuss et al., "A transport access chamber for the rat dorsal skin flap," *Microvascular Research*, 18:311–318; 1979.
Tan, "Pulsed dye laser treatment of adult port–wine stains," Chapter 6, pp. 83–99, in *Management and treatment of benign cutaneous vascular lesions*, Tan (ed.), Lea & Febiger, Philadelphia, 1992.
van Gemert et al., "Laser treatment of port wine stains," Chapter 23 in: *Optical–Thermal Response Of Laser–Irradiated Tissue*, Welch and van Gemert (eds), Plenum Press, New York, 789–829, 1995.
Vargas et al., "Use of an agent to reduce scattering in skin," *Lasers in Surgery & Medicine*, 24:133–141; 1999.
Vargas et al., "Use of osmotically active agents to alter properties of tissue: effects on the detected fluorescence signal measured through skin," *Lasers in Surgery & Medicine*, 29:213–220; 2001.
Vargas, "Reduction of Light Scattering in Biological Tissue: Implications for Optical Diagnostics and Therapeutics," Doctoral Dissertation, The University of Texas at Austin, 2001.

* cited by examiner

*Primary Examiner*—Vickie Kim
(74) *Attorney, Agent, or Firm*—Fulbright & Jaworski, LLP (57) ABSTRACT

Methods for treating maladies such as cutaneous vascular lesions. A patient in need of vascular lesion treatment is identified. A hyperosmotic agent is administered to a region adjacent the lesion. Blood flow velocity is slowed within the region using the hyperosmotic agent, and the lesion is exposed to laser radiation.

14 Claims, 6 Drawing Sheets

LASER TREATMENT OF CUTANEOUS VASCULAR LESIONS

This application claims priority to, and incorporates by reference, U.S. Provisional Patent Application Ser. No. 60/363,726 filed Mar. 12, 2002 entitled "Laser Treatment of Cutaneous Vascular Lesions."

BACKGROUND OF THE INVENTION

Aspects of this invention were made with government support of the National Science Foundation, grant number BES9986296. Further support has been provided by Texas Higher Education Coordinating Board, grant number BER-ATP-253. Accordingly, the government may have certain rights in this invention.

1. Field of the Invention

The present invention relates generally to biomedical engineering, imaging, medicine, and medical treatment. More particularly, it concerns clinical laser treatment of cutaneous vascular lesions using chemical agents that not only increase light penetration but also decrease blood flow velocity.

2. Description of Related Art

Cutaneous vascular lesions can be classified into two main categories. The first includes benign disorders, such as the hemangioma (a benign tumor consisting of a dense mass of blood vessels) and the cutaneous nevus (a congenital discoloration of a skin area, also called a strawberry or stork mark) [van Gemert et al., 1995; Mulliken, 1992]. The second category is made up of vascular malformations, where the lesion is caused by abnormal blood vessel pathology [Mulliken, 1992]. Included in this class of cutaneous vascular lesions is the port wine stain (PWS), a congenital lesion in which ectatic capillaries make an area appear a dark red color and produce raised nodules protruding above the normal skin surface. Another vascular malformation is leg telangiectasia, small, localized clusters of blood vessels sometimes found deep (millimeters) below the surface. Telangicctasis can also occur as an extensive network that is much more widespread [Goldman, 1992].

Some of these lesions, such as the port wine stain (PWS), can be quite traumatic for a patient, resulting in serious psychological and social problems [Lanigan et al., 1989; Tan, 1992; Morelli et al., 1992; Masciarelli, 1992; van Gemert, 1992]. When lesions are located near joints, lips, or the eyes they can also interfere with normal functions and lead to serious problems such as hypertrophy of skeletal tissue or more severe conditions [Mulliken, 1992]. Because the lesions become increasingly hypertrophic, early treatment is preferred.

Currently, the only accepted treatment for these vascular lesions is pulsed laser radiation at selected wavelengths that target the absorption characteristics of hemoglobin. By selecting the proper laser pulse duration, the process is referred to as selective photothermolysis. Blood vessels are damaged by the increase in temperature resulting from absorption of pulsed laser light. The objective is to permanently destroy the blood vessels comprising a cutaneous lesion, while sparing surrounding skin structures.

A number of shortcomings exist in current clinical treatments due to the lack of parameter optimization and sufficient delivery of light to deep lying blood vessels. Unfortunately, because the treatment parameters governing the effectiveness of laser therapies vary greatly from patient to patient, many instances of incomplete destruction of abnormal vessels and clearing of the lesion occur.

In general, low treatment success rates remain a problem with existing laser treatments of vascular lesions. This low success rate is due to at least two main limitations: (a) restrictions in the achievable penetration depth of light in biological tissue and (b) insufficient increase in blood vessel temperatures associated with high flow velocities.

The first limitation (limitation (a)) in the laser treatment of cutaneous vascular lesions involves rapid attenuation of incident light with depth. Attenuation of laser light in biological media occurs by absorption and scattering. In many cases, deep blood vessels in a lesion are not sufficiently heated by incident light due to competition from absorption and scattering by other tissue constituents. This competition for laser light decreases the fluence rate [$W/cm^2$] available for photocoagulation of a blood vessel. In view of this limitation, methodologies that decrease light attenuation and increase the penetration depth of incident light are desirable.

The second limitation (limitation (b)) in the laser treatment of vascular lesions involves the lack of control of blood flow velocity. Blood flow velocity has been shown to be an important factor that affects the success of vessel photocoagulation. Specifically Boergen, et al. have shown that complete flow cessation of blood in vessels before laser irradiation significantly decreases the fluences required to permanently destroy a blood vessel [Boergen et al., 1977]. Despite this realization, current laser treatment techniques have not been able to fully capitalize upon the benefits afforded by controlling blood flow velocity during treatment. In view of this limitation, methodologies that not only decrease light attenuation, but also decrease blood flow velocity would be desirable.

The referenced shortcomings of conventional methodologies mentioned above are not intended to be exhaustive, but rather are among many that tend to impair the effectiveness of previously known techniques concerning the laser treatment of cutaneous vascular lesions. Other noteworthy problems may also exist; however, those mentioned here are sufficient to demonstrate that methodology appearing in the art have not been altogether satisfactory and that a significant need exists for the techniques described and claimed herein.

SUMMARY OF THE INVENTION

Shortcomings of the prior art are reduced or eliminated by the techniques disclosed herein. These techniques are applicable to a vast number of applications, including but not limited to applications involving the laser removal of cutaneous vascular lesions.

Procedures described herein are able to reduce the laser dose required for irreversible photocoagulation of blood vessels in tissue. Each of the two main limitations of conventional techniques, discussed above, are addressed by using a specific class of chemical agents together with application of laser radiation to blood vessels. Required fluences for the permanent destruction of blood vessels in the skin are significantly lower with the techniques of this disclosure as compared to cases where no chemical agents are used. Experimental results substantiating the assertions of this disclosure are presented in the Examples section.

In a recent study, the inventors discovered that the addition of glycerol, and other chemical agents, to skin leads to changes in blood vessel morphology. In particular, glycerol alters the flow characteristics of blood in the skin. In the study, glycerol was added to the subdermal side of skin in which blood vessels were located 80–100 $\mu$m from the subdermal surface. Within twenty minutes, the flow in venules (approximately 100–400 μm in diameter) ceased. Over prolonged periods of exposure to glycerol, flow in arterioles ceased as well. When the skin was hydrated in a physiologic saline solution, flow in arterioles and venules returned to physiologic values. In the experience of the inventors, the addition of glycerol, and the other hyperosmotic agents described herein, to blood vessels did not result in any permanent vessel damage.

These recently-discovered morphological effects of glycerol (and other agents) on blood flow velocity, coupled with glycerol's ability to increase light transmission within turbid media (i.e., glycerol's "optical clearing" properties), serve as one basis for an effective, new methodology for vastly improved laser treatment of cutaneous vascular lesions. First, increased light penetration due to glycerol and other hyperosmotic agents allows for better localization of light on deep blood vessels that previously would not have been targeted. Second, decrease in blood flow velocity due to glycerol allows for significantly lower radiant light exposures to be used for blood vessel photocoagulation.

In one embodiment, the invention is a method for reducing the amount of radiation required to destroy a blood vessel of a cutaneous vascular lesion. The method involves administering a hyperosmotic agent to the blood vessel to slow blood flow velocity prior to exposure to laser radiation.

In another embodiment, the invention is a method of treating a cutaneous vascular lesion. A patient in need of vascular lesion treatment is identified. A hyperosmotic agent is administered to a region adjacent the lesion. Blood flow velocity is slowed within the region using the hyperosmotic agent, and the lesion is exposed to laser radiation.

In another embodiment, the invention is a method of destroying a blood vessel. A hyperosmotic agent is administered to the blood vessel to reduce blood flow velocity by at least 15%, and the blood vessel is exposed to an amount of laser radiation at least 15% less than an amount of radiation required to destroy a blood vessel in the absence of the administration of the hyperosmotic agent.

As used herein, "amount of radiation" simply means any measure of radiation being used to treat a lesion or other malady. In one embodiment, the "amount of radiation" may be measured with reference to energy per unit area, such as $J/cm^2$. As used herein, "adjacent" shall be interpreted broadly to mean not only "close to," but also overlapping with (completely or partially). Thus, an agent administered "adjacent" a region may be administered near or at that region.

Other features and associated advantages will become apparent with reference to the following detailed description of specific embodiments in connection with the accompanying drawings.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 2A and 2B are photographs in accordance with embodiments of the present disclosure. Preparation of a subdermal side of a hamster dorsal skin flap window is shown. Blood vessels are located approximately 80–100 μm from the near-surface. FIG. 2A shows native skin. FIG. 2B shows the same window preparation, twenty minutes following treatment with glycerol.

FIGS. 7A and 7B are photographs in accordance with embodiments of the present disclosure. Shown is the subdermal side of the control sample twenty-four hours after irradiations (applied to the epidermal surface) up to 16 $J/cm^2$. FIG. 7A is an amplitude image, and FIG. 7B is a Doppler image. Flow in both the arteriole and venule remains.

DESCRIPTION OF ILLUSTRATIVE EMBODIMENTS

U.S. Pat. No. 6,275,726 ("the '726 patent") entitled, "Methods of enhanced light transmission through turbid biological media" by Chan et al. is hereby incorporated by reference in its entirety.

The '726 patent involves a process to increase light transmission in biological tissue. The technique involves temporarily replacing tissue water with a fluid that has a refractive index closer to that of inter/intra cellular components. Subsequently, the amount of index mis-match between those components and the fluid environment is temporarily decreased. This, in turn, lowers the amount of random reflection and refraction which also reduces light scattering.

Although useful for the methodology it describes and claims, the '726 patent does not address problems associated with conventional laser techniques' inability to adequately control blood flow velocity. This inability, in turn, hinders the effective clinical laser treatment of cutaneous vascular lesions. Further, the '726 patent does not recognize that certain chemical agents may significantly affect blood flow velocity in a manner that can be exploited to greatly improve the treatment of cutaneous vascular lesions. In sum, the '726 patent does not recognize or describe the particular applications described and claimed herein that create a new clinical laser treatment protocol for cutaneous vascular lesions. This protocol not only reduces light attenuation but also controls blood flow velocity to effectively remove lesions using lasers exhibiting lower radiant light exposures.

The present disclosure describes methods for the laser treatment of cutaneous vascular lesions and other maladies. The techniques described herein are advantageous at least because they address shortcomings exhibited in the prior art—(a) light attenuation and (b) lack of control of blood flow velocity. Applications for these techniques are vast and include any situation in which a decreased blood flow velocity and/or reduced light attenuation is desired. In particular, the laser treatment of blood vessel lesions, including hyper-vascular lesions, benefits greatly. Examples of this type of treatment are port wine stains and leg telangiectasia. One aspect of embodiments of this disclosure involves the use of chemical agents to alter the optical properties of tissue in order to enhance the delivery of light to physiological targets in the skin (i.e., "optical clearing"). This aspect is based, at least in part, upon the findings of U.S. Pat. No. 6,275,726, which has been incorporated by reference and discusses how appropriate chemical agents may be used to optically alter biological tissue in a direction that increases the penetration-depth of light.

Another aspect of embodiments of this disclosure involves the use of chemical agents to alter the blood flow velocity of tissue. The chemical agents allow one to control the blood flow velocity; in particular, it has recently been discovered by the inventors that the application of appropriate agents may significantly reduce, or even halt, blood flow velocity in a reversible manner.

In combination, these two aspects, which would have seemed to be disparate and unrelated phenomena prior to this disclosure, provide the basis for drastically improved laser treatment techniques. Specifically, these two aspects in combination provide for an effective clinical laser treatment protocol for the removal of cutaneous vascular lesions.

In one embodiment, hyperosmotic chemical agents are used to significantly reduce the laser doses required to irreversibly destroy blood vessels of a vascular lesion. The method uses chemical agents that temporarily reduce scattering in biological tissue and reduce the velocity of blood in vessels. Based on the experimental results listed in the "Examples" section of this disclosure, a significant improvement in clinical treatment of hyper-vascular lesions is provided. In particular, the results reveal a significant reduction in the laser radiant exposures required to permanently destroy a blood vessel, both under direct irradiation conditions and when the laser beam is delivered to the skin epidermal surface and must travel through the dermis to reach blood vessels.

Different embodiments involve the application of different hyperosmotic chemical agents prior to laser irradiation of a vascular lesion. In one embodiment, a suitable hyperosmotic chemical agent is glycerol. In other embodiments, suitable hyperosmotic chemical agents may include, but are not limited to: dimethyl sulfoxide, sucrose, glucose (dextrose), propylene glycol, polyethylene glycol, hypaque sodium (diatrizoate sodium), or mannitol. Any of these agents may be used alone, or in combination with another one or more of the agents.

Suitable doses and concentrations of hyperosmotic chemical agents may be found by reference to U.S. Pat. No. 6,275,726. In different embodiments, agents may be diluted and still achieve the same or similar results discussed herein; in particular, in different embodiments, one may dilute glycerol (down to 25%) or glucose (down to 10%).

Suitable techniques to deliver the hyperosmotic chemical agents may be found by reference to U.S. Pat. No. 6,275,726, although it will be understood that any other suitable delivery technique may be exploited including, but not limited to, a variety of transdernal techniques. One suitable technique for delivery is injection. In different embodiments, the injection may be accomplished by a fine hypodermic needle or a high velocity jet. Another suitable technique involves use of a transdermal drug delivery device. Such suitable techniques include, but arc not limited to: (1) tape stripping the surface of skin to remove a small area of epidermis (a technique in common use), (2) use of ablative methods—such as laser ablation techniques—to create micro-holes in the skin down to the dermis or subdermis, (3) chemical peels, (4) mechanical debridement, (5) ultrasound-enhanced techniques, (6) electroporation, or (7) iontophoresis to aid transdermal diffusion of chemical agents.

After the desired optical and morphological changes are induced on the tissue through the delivery and application (e.g., transdermal delivery or injection) of one or more hyperosmotic chemical agents, laser radiation may be applied to the lesion. The chemical agents both reduce scattering in the biological tissue, and also lead to the reduction and/or cessation of flow in arterioles and venules. The changes allow laser energy to be more directly applied to the vessels and, concurrently, reduce the required energy to destroy a given vessel.

Accordingly, the techniques of this disclosure solve the once-difficult balancing problem of being able to deliver sufficient laser energy to a targeted blood vessel to destroy the vessel without damage to the epidermis and dermis by making it possible to use lower power lasers (and/or lower laser doses) to cause irreversible photocoagulation. The techniques reduce or even eliminate the necessity of multiple treatments to coagulate vessels. Advantageously, the observed optical, morphological, and physiological effects due to application of the chemical agents to skin are reversible with simple hydration of the tissue.

Figure 1:
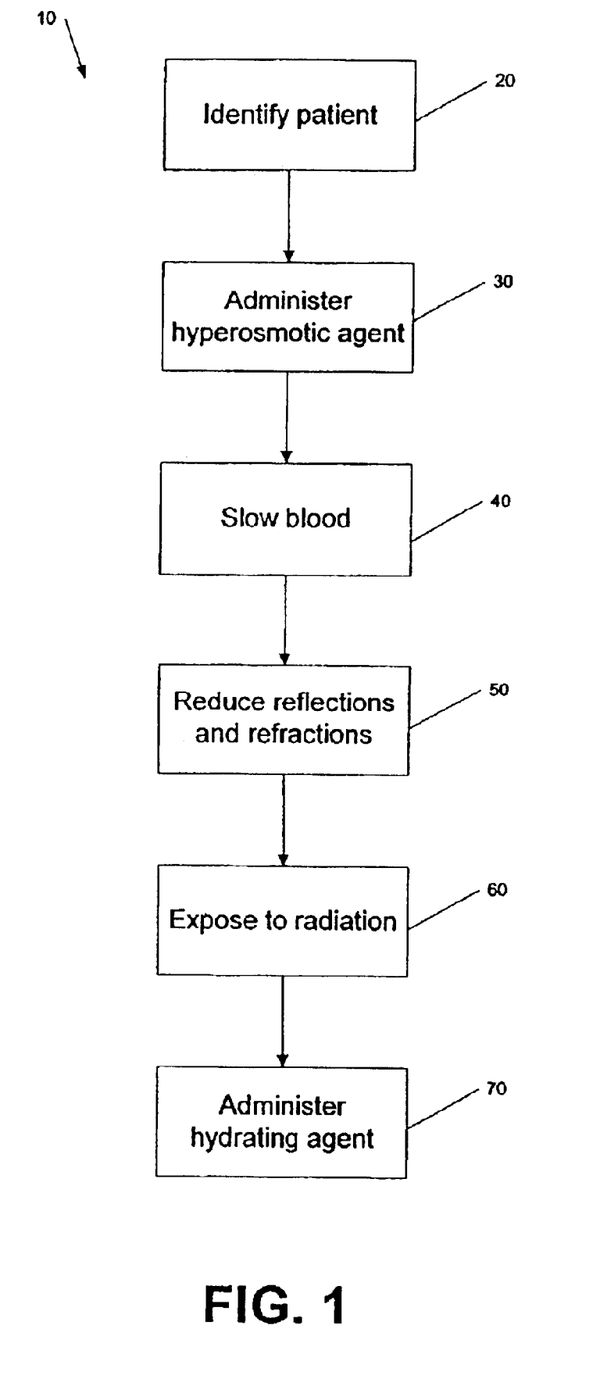
FIG. 1 is a flowchart illustrating exemplary embodiments of the present disclosure.

Turning to FIG. 1, there is shown a flowchart illustrating general, exemplary embodiments of the present disclosure. In step 20, a patient is identified. In one embodiment, the patient may be in need of vascular lesion treatment. In other embodiments, the patient may be in need of other treatments that would benefit from a reduction in light reflection/refraction and/or decreased blood flow velocity. In one embodiment, the patient may be human, while in other embodiments, the patient may be any other type of living organism.

In step 30, one or more hyperosmotic agents are administered to the patient. In the case of vascular lesions, an agent is administered to a region adjacent the lesion—at the lesion itself or near the region. In one embodiment, the agent may be administered at the site of one or more blood vessels to be permanently photocoagulated, or destroyed, by laser treatment. The administration of the agent may be done as is known in the art. In one embodiment, injection by a hypodermic needle or a high velocity jet may be used. In other embodiments, tape stripping, ablation, chemical peel, electroporation, iontophoresis, mechanical debridement, or other transdermal delivery method may be used. The hyperosmotic agent may include any of the agents discussed herein, including those discussed in U.S. Pat. No. 6,275,726.

In step 40, blood flow velocity is reduced by way of the administration of the hyperosmotic agent. In one embodiment, this reduction in blood flow velocity may be at least 15%. In particular, the reduction in blood flow velocity may be about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%. To measure the reduction in blood flow velocity, one may measure the blood flow velocity before and after application of a hyperosmotic agent.

In step 50, light reflection and refraction are reduced among cellular components at or about a region to be treated to enhance light transmission. This "optical clearing" comes about by way of the administration of the hyperosmotic agent, as discussed in U.S. Pat. No. 6,275,726.

In step 60, the area to be treated is exposed to radiation, such as laser radiation. The amount of radiation applied to the area may vary greatly depending upon the application. In embodiments involving the treatment of cutaneous vascular lesions, the administration of one or more hyperosmotic agents in step 30 advantageously lowers the amount of radiation required to treat the lesions (i.e., to permanent photocoagulate, or destroy, blood vessels associated with the lesions). In fact, the reduction in laser radiation may be at least 15%. In particular, the reduction in radiation amount may be about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40% , 41%, 42%, 43%, 44%, 45%, 46%, 47%, 48%, 49%, 50%, 51%, 52%, 53%, 54%, 55% , 56%, 57%, 58%, 59%, 60%, 61%, 62%, 63%, 64%, 65%, 66%, 67%, 68%, 69%, 70% , 71%, 72%, 73%, 74%, 75%, 76%, 77%, 78%, 79%, 80%, 81%, 82%, 83%, 84%, 85% , 86%, 87%, 88%, 89%, 90%, 91%, 92%, 93%, 94%, or 95%. To measure the reduction in blood flow velocity, one may measure the energy per area required to treat a lesion with and without the administration of a hyperosmotic agent. In one embodiment involving the treatment of lesions, a suitable range of radiation may be between about 0.1 and about 20 J/cm$^2$. In one embodiment, the source of laser radiation may be light sources, including lasers, in the wavelength range of about 450–1100 nm. Typical sources include, but are not limited to cw (continuous wave) and pulsed diode lasers, dye lasers, solid state lasers, and gas lasers. In one embodiment delivery may be through optical fibers. In other embodiments, any other suitable source of radiation may be used.

In step 70, a hydrating agent is administered to the area being treated. The purpose of the hydrating agent is to flush the hyperosmotic agent from the area and to return the area being treated as close as possible back to its normal, pre-treatment state, excluding the status of blood vessels. The administration of the hydrating agent may be accomplished by any of the means used to administer the hyperosmotic agent(s), including injection. In one embodiment, the hydrating agent may include saline. Other hydrating agents and techniques are discussed in U.S. Pat. No. 6,275,726.

Figure 5:
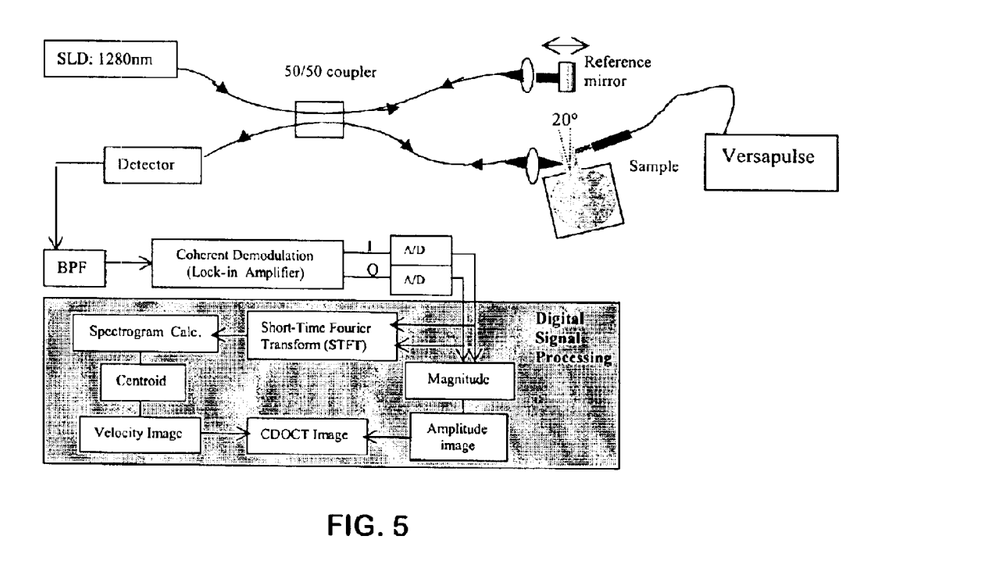
FIG. 5 is a schematic diagram of equipment suitable for carrying out embodiments of the present disclosure.

FIG. 5 shows one suitable apparatus for visualizing the effects of the techniques described herein, such as those illustrated in FIG. 1. FIG. 5 shows an optical setup of a color Doppler optical coherence tomography system (CDOCT). CDOCT is a light imaging device that acquires cross-sectional, in-depth images of biological tissue [Izatt et al., ]. Besides providing images of tissue structure, CDOCT reveals blood vessels by detecting Doppler shifts due to moving blood. After imaging, samples may be irradiated in place using equipment such as a frequency-doubled Nd:YAG laser (Versapulse V, Coherent). Technical specifications of the device are described: A superluminescent diode (SLD) centered at 1290 nm is used as the light source. The light from the SLD is split into a reference arm (incident on a reference mirror) and a sample arm (incident on the sample). The probing beam is incident on the dorsal window, which may be tilted at $20\mu$ with respect to the vertical to obtain Doppler information. The light from the sample and the reference mirror recombine and form an interference signal. The envelope of the interference signal may be filtered with a bandpass filter (BPF). The signal is coherently demodulated in a lock-in amplifier. The backscattered magnitude (I) and the phase information (Q) undergo digital signal processing in a computer. Labview software [Izatt, Case Western University] may be used to process and display amplitude (magnitude) and Doppler (velocity) images.

With the benefit of the present disclosure, those having skill in the art will comprehend that techniques claimed herein and described above may be modified and applied to a number of additional, different applications, achieving the same or a similar result. The claims attached hereto cover all such modifications that fall within the scope and spirit of this disclosure.

The following examples are included to demonstrate specific embodiments of this disclosure. It should be appreciated by those of skill in the art that the techniques disclosed in the examples that follow represent techniques discovered by the inventors to function well in the practice of the invention, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the invention.

EXAMPLES

In these examples, the inventors use chemical agents for reducing the applied laser radiant exposure required to permanently destroy blood vessels. The technique has been demonstrated both in direct blood vessel irradiations, and also on blood vessels located hundreds of microns beneath the epidermal surface of in vivo skin. Evidence is presented that demonstrates the treatment of skin with agents such as glycerol prior to laser radiation leads to a significant decrease in the delivered radiant exposures required to permanently destroy a blood vessel, compared to control cases where treatment with agents such as glycerol did not occur.

MATERIALS AND METHODS

Animal Model

Hamsters were anesthetized with a 4:3 mixture of Ketamine (20 mg/ml):Rompun (100 mg/ml) and 0.15 ml/100 g body weight of the solution was delivered IP. The rodent dorsal skin flap window preparation first developed by Papenfuss et al. was used as an in vivo animal model to demonstrate the effect of glycerol on photocoagulation of blood vessels. This in vivo model allows the simultaneous observation of the epidermal and subdermal sides of the skin while maintaining hydration and function [Papenfuss et al., 1979]. The preparation has been used as an in vivo model for optical imaging blood vessels on the subdermal side of skin while maintaining access to the epidermis [Barton et al., 1998, Vargas et al., 2001].

The preparation includes shaving and epilating the entire dorsal area of a hamster. The skin is pulled away from the body along the dorsal midline and sutured to a vertical c-clamp. A circular region 1 cm in diameter is cut from one single thickness of skin, exposing the subdermal side of the opposing thickness of skin. An aluminum chamber is sutured to both sides of the skin, and glass is placed over the cutout section to prevent the tissue from dehydrating on the subdermal side. During the experiments, this glass is removed for improved imaging, and hydration is maintained with application of physiological saline.

Blood vessels in the skin of the dorsal window preparation are located in the subdermal fat and connective tissue layers approximately 400–700 $\mu$m beneath the epidermal surface and about 80–100 $\mu$m from the exposed subdermal surface of a 100 g hamster. Arterioles and venules in the dorsal window preparation range in diameter between about 50–500 $\mu$m in inner diameter, with the main arteriole and venule about 350–500 $\mu$m in diameter.

In vivo Application of Glycerol

Figure 2A:
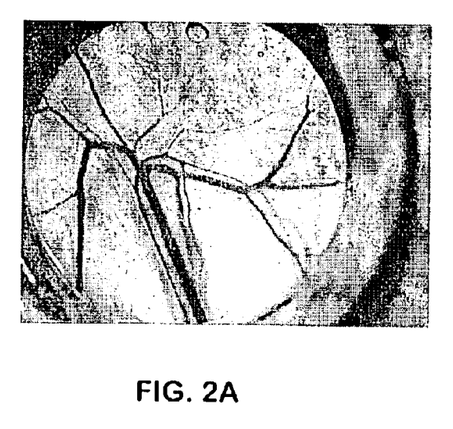
Figure 2B:
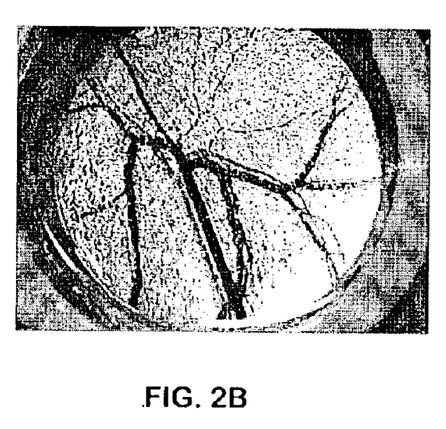

Anhydrous glycerol was applied to the subdermal side of the dorsal skin flap window preparation. The subdermal side of the window preparation contains a well approximately 2 mm deep and 1 cm in diameter placed directly over the exposed subdermal skin. A small opening at the bottom allows the flow of glycerol out of the well. This well was filled with glycerol and continually refilled for a total time of twenty minutes. Any remaining glycerol was removed from the well at the end of twenty minutes. An example window preparation shown from the subdermal side before and after the application of glycerol is shown in FIG. 2.

Subdermal Irradiations

Figure 3:
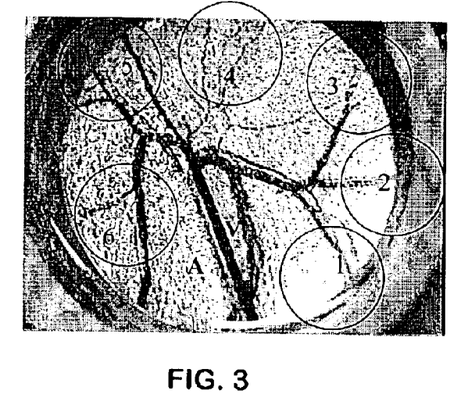
FIG. 3 is a photograph in accordance with embodiments of the present disclosure. The locations of subdermal blood vessel irradiations in one dorsal skin flap window-preparation are shown.

Subdermal irradiations allowed for the direct irradiation of blood vessels in the rodent dorsal skin flap window preparation. Direct irradiations of blood vessels following treatment with glycerol were performed to demonstrate the benefits of a decrease in blood flow velocity due to chemical agents. A total of 46 venules and 38 arterioles were irradiated directly in six window preparations following application of glycerol with radiant exposures ranging from 0.3 J/cm$^2$ to 7.5 J/cm$^2$. Three to six irradiations were performed on each window preparation depending on the anatomical structure of the microvasculature. For instance, in the window preparation of FIG. 3, six areas were irradiated (shown by the circles) to target individual arteriole-venule pairs.

Venules ranged in diameter from 50 to 200 micrometers. Arteriole diameters ranged from 20 to 140 micrometers. Each arteriole-venule pair was irradiated a single time with a single pulse from a Versapulse V Vascular (Coherent, Santa Clara, Calif.) laser at 532 nm with a pulse duration of 10 ms and spot size of 3 mm. The window preparation was viewed and recorded through a surgical microscope (Wild Leitz M650, Germany) prior to, during, and following irradiation. The window preparation was observed twenty-four hours after laser irradiation to assess whether permanent coagulation occurred for each vessel irradiated.

Since previous studies have revealed that the fluences required to permanently destroy a blood vessel depends on size and type (arteriole vs. venule) [Kimel et al., 1994; Barton, 1998], data analysis for venules and arterioles was done separately, and for each type, vessels were categorized according to inner diameter. Venules were categorized in four groups (50–80 $\mu$m, 80–110 $\mu$m, 10–140 $\mu$m, and 140–200 $\mu$m diameter) and arterioles into three groups (20–50 $\mu$m, 50–80 $\mu$m, and 80–110 $\mu$m).

Yes/no (0/1) grading of vessel destruction by photocoagulation after twenty-four hours was used to perform probit analysis on the data assuming a sigmoid probability distribution, resulting in 50% probability for threshold radiant exposures (RE50) for vessels of a given size category and type [Cain et al., 1996].

Epidermal Irradiations

While the subdermal irradiations were done to show that the resulting decrease in blood flow velocity by glycerol allows for a substantial decrease in laser doses to destroy vessels, epidermal irradiations were performed to demonstrate how the technique could be carried out clinically. In this set of experiments, three dorsal skin flap window preparations were treated with glycerol on the subdermal side of the skin. Then, the main arteriole-venule pair (such as the one labeled A and V in FIG. 3) was irradiated from the epidermal side to determine the approximate range of radiant exposures required to permanently destroy blood vessels in skin treated with glycerol. Since no published data exists for direct comparison with controls, two native hamster dorsal skin flap window preparations were irradiated from the epidermal side as well.

The skin surrounding the main arteriole-venute pair in each window preparation was first imaged using Color Doppler optical coherence tomography (CDOCT) (see FIG. 5). The skin was imaged from the subdermal side since these blood vessels are located approximately 100 $\mu$m from the subdermal surface, allowing for accurate determination of vessel flow and size characteristics. In the case of control samples (2), the vessels were irradiated from the epidermal side immediately after imaging the native skin. This was achieved by applying a single pulse from a 532 nm, 3 mm spot size, 10 ms pulse duration laser (Versapulse V, Coherent) to the skin without altering its position relative to the CDOCT sample probe. The experimental setup is illustrated in FIG. 5.

The skin was imaged again to assess changes to blood flow. In the first control sample, if no changes were observed to occur, the skin was radiated with a higher radiant exposure one hour later. If any changes in flow or vessel size were observed, the skin was not irradiated again and was imaged after 24 hours. In all, 5 pulses were delivered ranging in radiant exposure from 4.13 J/cm$^2$ to 16 J/cm$^2$, the maximum allowable for the laser parameters used. In the second control sample, only a single pulse was delivered with a radiant exposure of 12 J/cm$^2$.

In the other three samples, glycerol was applied to the subdermal side of the window preparation for twenty minutes after imaging the native skin with CDOCT. The optically cleared skin was then imaged again using CDOCT. Laser pulses were applied in the same manner described above and the skin was re-imaged after twenty-four hours to assess if permanent vessel closure occurred.

RESULTS

Subdermal Irradiations

Figure 4:
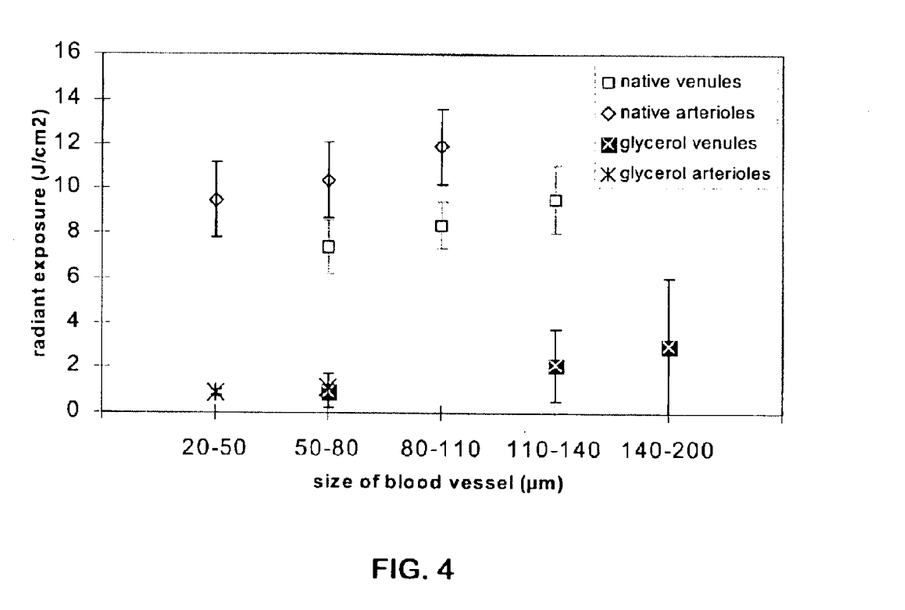
FIG. 4 is a graph showing results in accordance with embodiments of the present disclosure. This figure shows RE50 (radiant exposures which have been found through statistical analysis of the experimental data to result in a 50% probability of permanent vessel coagulation) values for permanent blood vessel coagulation using a 532 nm laser (10 ms pulse duration, 3 mm spot size) applied to the subdermal side of skin. Two experimental conditions are represented in this plot. Subdermal irradiations on native skin are summarized in the "native venules" and "native arterioles" data points. Subdermal irradiations conducted on skin in which anhydrous was applied to the subdermal side are shown by the "glycerol venules" and "glycerol arterioles" points.

The resulting RE50 values for permanent vessel destruction are summarized in FIG. 4 for arterioles and venules in skin treated with glycerol prior to irradiations. Results are compared to values from previously published results on subdermal irradiations performed on dorsal windows not treated with glycerol [Barton et al., 1998] in FIG. 4. Due to the small number of irradiations compared to the number of parameters (vessel size and type), there was insufficient data to estimate the ED50 values for arterioles and venules 80–110 $\mu$m in diameter.

Epidermal Irradiations

Figure 6A:
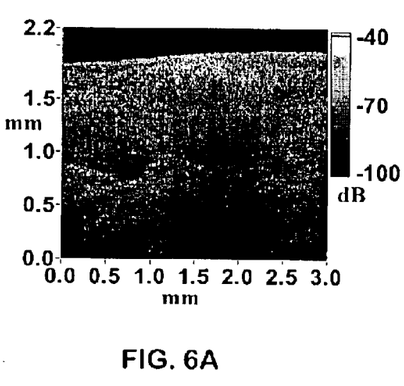
FIGS. 6A and 6B are photographs in accordance with embodiments of the present disclosure. Shown are amplitude (FIG. 6A) and Doppler (FIG. 6B) images of skin in the hamster dorsal skin flap window-preparation. The skin shown is a control sample prior to irradiation. The surface at the top is the subdermal connective tissue.
Figure 6B:
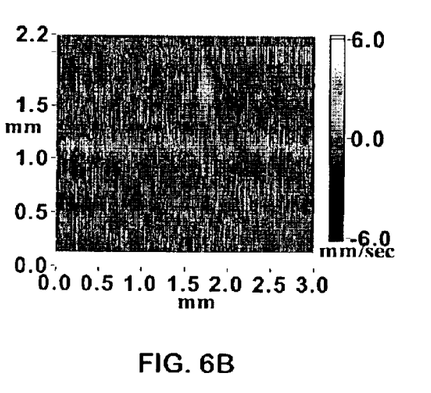
Figure 7A:
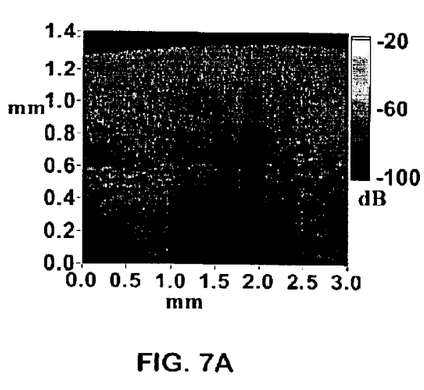
Figure 7B:
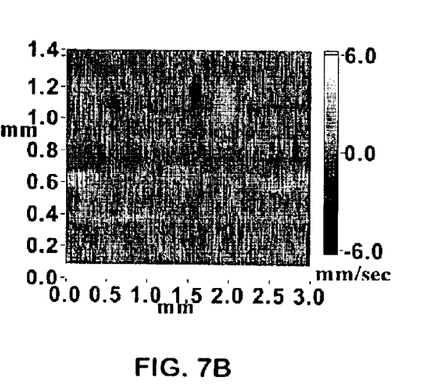

The CDOCT amplitude and Doppler images from the first control sample prior to irradiations are shown in FIG. 6. The amplitude image represents backscattered light from the tissue—a cross-section of the skin is shown. The Doppler image represents frequency-shifted light from scatterers in the skin. While one cannot identify blood vessels in the amplitude image, an arteriole and venule are identified in the Doppler image. The arteriole (A) diameter is 225 $\mu$m, and the venule (V) diameter is 470 $\mu$m. They are located approximately 80 $\mu$m from the subdermal surface (the first interface in the top of the amplitude scan) and 750 $\mu$m from the epidermal surface (not shown here). Although this sample was repeatedly irradiated with radiant exposures starting at 4.13 J/cm$^2$ and ending with 16 J/cm$^2$, twenty-four hours later flow remains in both vessels (FIG. 7).

In the second control sample a single pulse (12 J/cm$^2$) was unsuccessful in leading to permanent flow cessation of either an arteriole (290 $\mu$m) or venule (460 $\mu$m), which were located 500 $\mu$m below the epidermal surface of the skin (100 $\mu$m from the subdermal surface).

Figure 8A:
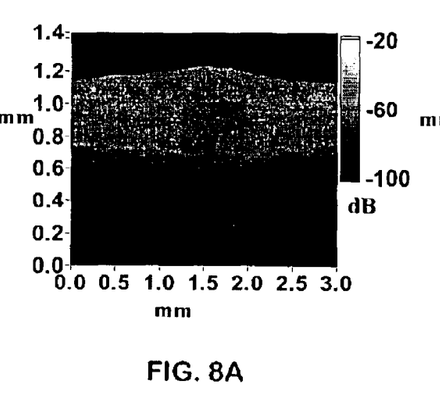
FIGS. 8A and 8B are photographs in accordance with embodiments of the present disclosure. Shown are amplitude (FIG. 8A) and Doppler (FIG. 8B) images of a native skin sample imaged from the subdermal side. An arteriole and venule are identified in the Doppler image.
Figure 8B:
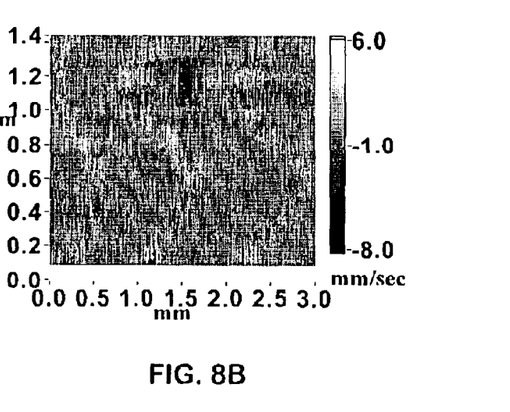

In the three window preparations where glycerol was applied prior to irradiation from the epidermal side, blood vessels on the subdermal side of the skin were successfully destroyed with radiant exposures as low as 1.6 J/cm$^2$. One such example follows. The native skin of one rodent window preparation is shown in FIG. 8. The arteriole diameter is 250 $\mu$m, while the venule has a diameter of 300 $\mu$m. They are located 450 $\mu$m from the epidermal surface.

Figure 9A:
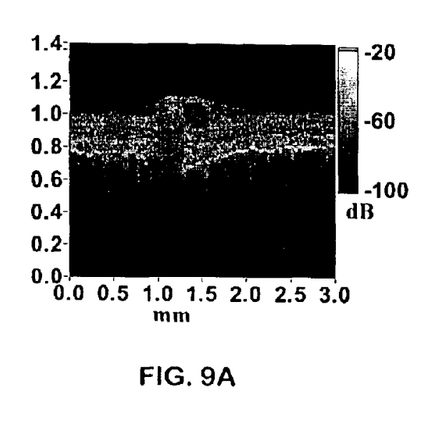
FIGS. 9A and 9B are photographs in accordance with embodiments of the present disclosure. Shown are amplitude (FIG. 9A) and Doppler (FIG. 9B) images of a skin sample treated with glycerol for twenty minutes and imaged from the subdermal side. The arteriole and venule are identified in the amplitude image; however, no flow remains as can be seen from the lack of Doppler shifts in the Doppler image.
Figure 9B:
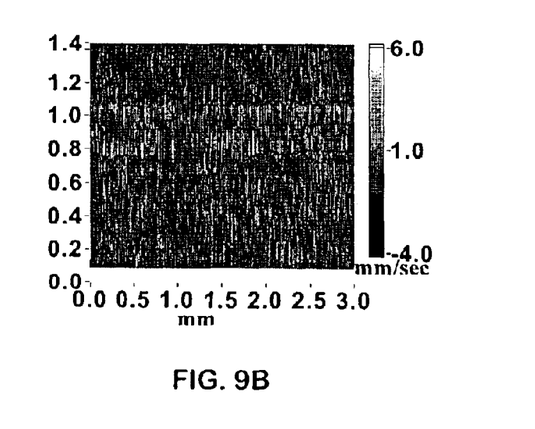
Figure 10A:
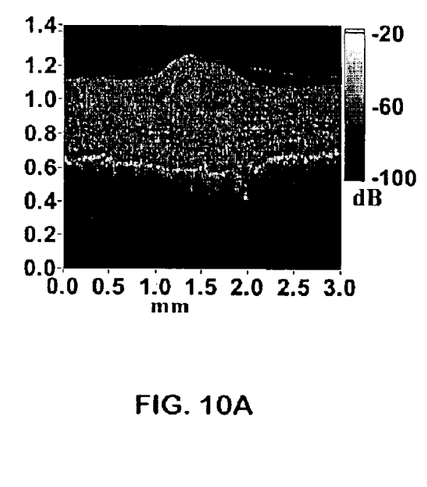
FIGS. 10A and 10B are photographs in accordance with embodiments of the present disclosure. Shown are amplitude (FIG. 10A) and Doppler (FIG. 10B) images showing hamster skin twenty-four hours after irradiation with 1.6 $J/cm^2$ following treatment with glycerol. Permanent coagulation has been achieved in both blood vessels.
Figure 10B:
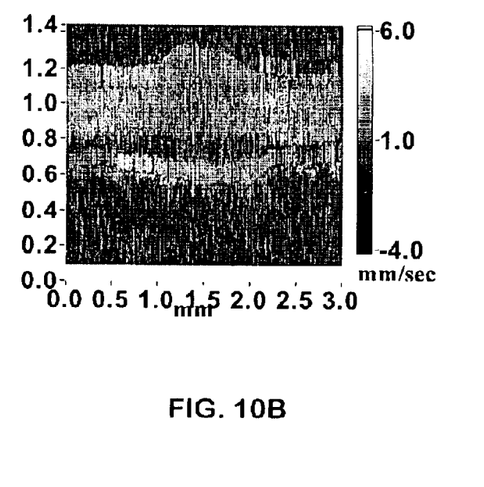

The same skin is again shown after treatment with glycerol for twenty minutes (FIG. 9). The Doppler image of FIG. 9 shows that flow does not remain in either the arteriole or venule. This result is typical as has been observed in a previous study [Vargas, 2001]. That study showed that flow cessation after the treatment with glycerol alone is not permanent (upon hydration the skin and blood vessels return to their native state). A single pulse (1.6 J/cm$^2$) was applied from the subdermal side of the skin in FIG. 9. Twenty-four hours later, flow has not returned to either vessel (FIG. 10), despite hydration of the skin.

In another preparation, successful permanent coagulation using glycerol was achieved using a radiant exposure of 4.13 J/cm$^2$. In this case the vessels (200 $\mu$m arteriole and 410 $\mu$m venule) were located 680 $\mu$m below the epidermal surface in the native skin and almost 400 $\mu$m in the skin treated with glycerol. Finally, in the third case 4.95 J/cm$^2$ applied to skin with a 300 $\mu$m arteriole and 390 $\mu$m venule, only the venule was successfully coagulated. In this case, the vessels were located 615 $\mu$m from the epidermal surface of the native skin and 300 $\mu$m in the glycerol-treated case.

DISCUSSION

Subdermal Irradiations

Because in subdermal irradiations, blood vessels of the skin were irradiated directly with no overlying tissue layers present, the data of FIG. 4 indicates that the morphological effects of glycerol on cutaneous blood vessels (specifically, the decrease in blood flow velocity) considerably aids in their permanent destruction by laser radiation. Comparison with previously published results [Barton et al., 1998] indicate that glycerol reduces radiant exposures required for permanent vessel destruction by a factor of 10 for arterioles and a factor of 5–8 for venules. The results of this experiment lead us to conclude that radiant exposures required to directly destroy vessels of a given type and size were drastically reduced by using glycerol to reduce or cause the cessation of blood flow in subdermal blood vessels.

Epidermal Irradiations

These results appear to indicate that the techniques discussed herein allow use of lower laser fluences when treating cutaneous blood vessel lesions. The studies of the inventors indicate that the decrease in laser fluences and increase in depth penetration of light afforded by these techniques may have a significant, lasting impact on the clinical laser treatment of cutaneous vascular lesions.

CONCLUSION

The presented data offers experimental support of using glycerol and other "optical clearing" agents that control flow velocity to enhance the laser treatment of cutaneous vascular lesions. This method may significantly impact clinical laser procedures not only for the treatment of cutaneous vascular lesions, but also for any malady whose treatment would benefit from increased light penetration and the reduction in blood flow velocity.

With the benefit of the present disclosure, those having skill in the art will comprehend that techniques claimed herein may be modified and applied to a number of additional, different applications, achieving the same or a similar result. For example, techniques of this disclosure may be applied to, for example, the treatment of blood vessels endoscopically—as in a stomach ulcer, etc. In such an application, topical application may be achieved without modifying the tissue. The claims attached hereto cover all such modifications that fall within the scope and spirit of this disclosure.

REFERENCES

Each of the following references is hereby incorporated by reference in its entirety:

U.S. Pat. No. 6,275,726

Barton J. K., Predicting Dosimetry for Laser Coagulation of in vivo Cutaneous Blood Vessels, Doctoral Dissertation, The University of Texas at Austin, 1998.

Boergen K. P., Bimgruber R., Gabel V. P., Hillenkamp F., "Experimental studies on controlled closure of small vessels by laser irradiation," Lasers in Surgery, Medicine, and Biology Proceedings, 1977.

Cain C. P., Noojin G. D., Manning L., A comparison of various probit methods for analyzing yes/no data on a log scale, Report AL/OE-TR-1996-0102, U.S.A.F. Armstrong Laboratory, Brooks Air Force Base, Texas (1996).

van Gemert M. J. C., Welch A. J., Pickering J. W., Tan O. T., "Laser treatment of port wine stains," Chapter 23 in: Optical-thermal response of laser-irradiated tissue, Welch A. J., van Gemert M. J. C., editors, Plenum Press, New York, 1995.

Goldman M. P., "Leg Veins: Pathogenesis, Sclerotherapy, and Lasers," Chapter 13, in Tan O. T., editor, Management and treatment of benign cutaneous vascular lesions, O. T. Tan, ed., Lea & Febiger, Philadelphia, 1992.

Izatt J. A., Kulkarni M. D., Yazdanfar S., Barton J. K., Welch A. J., "In vivo color Doppler flow imaging of picoliter blood volumes using optical coherence tomography," *Optics Letters*, 22: 1439–1441, 1997.

Lanigan S. W., Cotterill J. A., "Psychological disabilities amongst patients with port wine stains," *British Journal of Dermatology*, 21: 209–215, 1989.

Kimel S., Svaasand L. O., Hammer-Wilson M., Schell M. J., Milner T. E., Nelson J. S., Berns M. W., "Differential vascular response to laser photothermolysis," Journal of Investigative Dermatology, 103: 693–700, 1994.

Masciarelli P. C., "Living with a port-wine birthmark," Chapter 14, in: Management and treatment of benign cutaneous vascular lesions, Tan O. T., ed., Lea & Febiger, Philadelphia, 1992.

Mulliken J. B., "The classification of vascular birthmarks," Chapter 1 in Management and treatment of benign cutaneous vascular lesions, Tan O. T., ed., Lea & Febiger, Philadelphia, 1992.

Papenfuss H. D., Gross J. F., Intaglietta M., Treese F. A., A transport access chamber for the rat dorsal skin flap. Microvascular Research, 8:311–318; 1979.

Tan O. T., "Pulsed dye laser treatment of adult port-wine stains," Chapter 6 in: Management and treatment of benign cutaneous vascular lesions, O. T. Tan, ed., Lea & Febiger, Philadelphia, 1992.

Vargas G., Reduction of Light Scattering in Biological Tissue: Implications for Optical Diagnostics and Therapeutics, Doctoral Dissertation, The University of Texas at Austin, 2001.

Vargas G., Chan E. C., Barton J. K., Rylander H. G. III, Welch A. J., "Use of an agent to reduce scattering in skin," Lasers in Surgery & Medicine, 24:133–141; 1999.

Vargas G., Chan K. F., Thomsen S. L., Welch A. J., "Use of osmotically active agents to alter optical properties of tissue: effects on the detected fluorescence signal measured through skin," Lasers in Surgery & Medicine, 29:213–220; 2001.

What is claimed is:

1. A method of treating a cutaneous vascular lesion, comprising:

identifying a patient in need of vascular lesion treatment;

administering a hyperosmotic agent to a region adjacent the lesion;

slowing blood flow velocity within the region using the hyperosmotic agent; and exposing the lesion to laser radiation.

2. The method of claim 1, wherein the patient is human.

3. The method of claim 1, wherein administering comprises injection by a hypodermic needle or a high velocity jet.

4. The method of claim 1, wherein administering comprises tape stripping, ablation, chemical peel, mechanical debridement, electroporation, ultrasound, or iontophoresis.

5. The method of claim 1, wherein the hyperosmotic agent comprises glycerol.

6. The method of claim 1, wherein the hyperosmotic agent comprises dimethyl sulfoxide, sucrose, glucose (dextrose), propylene glycol, polyethylene glycol, hypaque sodium (diatrizoate sodium), or mannitol.

7. The method of claim 1, wherein the region adjacent the lesion overlaps the lesion.

8. The method of claim 1, wherein slowing blood flow velocity comprises slowing blood flow velocity by at least 15%.

9. The method of claim 1, wherein the blood flow velocity is slowed to zero.

10. The method of claim 1, wherein exposing the lesion to laser radiation comprises exposing the lesion to an amount of radiation sufficient to destroy a blood vessel, the amount of radiation being at least 15% less than an amount of radiation required to destroy a blood vessel in the absence of the administration of the hyperosmotic agent.

11. The method of claim 1, wherein exposing the lesion to laser radiation comprises irradiating the lesion with an energy per area between about 0.2 J/cm$^2$ and about 6 J/cm$^2$.

12. The method of claim 1, further comprising reducing light reflection and refraction among cellular components within the region, using the hyperosmotic agent, to enhance light transmission through the region.

13. The method of claim 1, further comprising delivering a hydrating agent within the patient and to a region adjacent the lesion.

14. The method of claim 13, wherein the hydrating agent comprises saline.

* * * * *